(12) United States Patent
Winter

(10) Patent No.: US 11,994,467 B2
(45) Date of Patent: May 28, 2024

(54) ARRANGEMENT AND METHOD FOR PCR WITH MULTI-CHANNEL FLUORESCENCE MEASUREMENT FOR SPATIALLY DISTRIBUTED SAMPLES

(71) Applicant: Analytik Jena GmbH, Jena (DE)

(72) Inventor: Stefan Winter, Dornburg-Camburg (DE)

(73) Assignee: Analytik Jena GmbH+Co. KG, Jena (DE)

(*) Notice: Subject to any disclaimer, the term of this patent is extended or adjusted under 35 U.S.C. 154(b) by 192 days.

(21) Appl. No.: 17/249,653

(22) Filed: Mar. 9, 2021

(65) Prior Publication Data
US 2021/0285878 A1 Sep. 16, 2021

(30) Foreign Application Priority Data
Mar. 12, 2020 (DE) ...................... 10 2020 106 865.4

(51) Int. Cl.
*G01N 21/64* (2006.01)
*C12Q 1/686* (2018.01)

(52) U.S. Cl.
CPC ......... *G01N 21/6428* (2013.01); *C12Q 1/686* (2013.01); *G01N 2021/6439* (2013.01)

(58) Field of Classification Search
CPC ....... G01N 21/6428; G01N 2021/6439; G01N 21/0332; G01N 2021/6417; G01N 21/6452; G01N 2021/6484; C12Q 1/686
See application file for complete search history.

(56) References Cited

U.S. PATENT DOCUMENTS

| | | | |
|---|---|---|---|
| 5,449,621 A * | 9/1995 | Klein | .................... G01N 15/042 356/426 |
| 5,589,351 A | 12/1996 | Harootunian | |
| 10,393,659 B2 | 8/2019 | Furlan | |

(Continued)

FOREIGN PATENT DOCUMENTS

| CN | 101189505 A | 5/2008 |
|---|---|---|
| DE | 102006036171 A1 | 1/2008 |

(Continued)

*Primary Examiner* — Samuel P Siefke
*Assistant Examiner* — Henry H Nguyen
(74) *Attorney, Agent, or Firm* — Christopher R. Powers; Endress+Hauser (USA) Holding, Inc.

(57) ABSTRACT

An arrangement and method for polymerase chain reaction with multi-channel fluorescence measurement includes two heating elements, each including a sample receptacle for receiving a sample carrier, wherein the sample receptacles each have a plurality of cavities; two measuring heads, each movable relative to the heating elements, wherein each measuring head is configured such that excitation light is coupled into each of the cavities and fluorescence light can be coupled out from the cavities; a fluorescence unit including: a rotatable carrier; at least one optical module disposed on the carrier and configured to generate the excitation light having at least one wavelength; and a detection unit for detecting a fluorescence in the cavities; and a coupling module configured for guiding the excitation light from the fluorescence unit to the measuring heads and for guiding the fluorescence light from the measuring heads to the fluorescence unit.

9 Claims, 3 Drawing Sheets

(56) References Cited

U.S. PATENT DOCUMENTS

| | | | |
|---|---|---|---|
| 2007/0009382 A1* | 1/2007 | Bedingham | G01N 21/6428 422/63 |
| 2012/0104280 A1* | 5/2012 | Manian | G01N 21/6428 250/459.1 |
| 2012/0190034 A1 | 7/2012 | Tajina | |
| 2014/0045186 A1 | 2/2014 | Gubatayao et al. | |
| 2018/0037930 A1 | 2/2018 | Nammoku et al. | |

FOREIGN PATENT DOCUMENTS

| | | | | |
|---|---|---|---|---|
| DE | 102006036171 B4 | 10/2008 | | |
| DE | 102007030347 A1 | 1/2009 | | |
| DE | 102009044795 B3 | 4/2011 | | |
| WO | 0196837 A1 | 12/2001 | | |
| WO | WO-0196837 A1 * | 12/2001 | | G01N 21/6452 |
| WO | 2005068976 A2 | 7/2005 | | |
| WO | 2006052682 A2 | 5/2006 | | |
| WO | 2008011875 A1 | 1/2008 | | |
| WO | 2010022417 A1 | 3/2010 | | |
| WO | 2011054353 A1 | 5/2011 | | |

* cited by examiner

ARRANGEMENT AND METHOD FOR PCR WITH MULTI-CHANNEL FLUORESCENCE MEASUREMENT FOR SPATIALLY DISTRIBUTED SAMPLES

CROSS-REFERENCE TO RELATED APPLICATION

The present application is related to and claims the priority benefit of German Patent Application No. 10 2020 106 865.4, filed on Mar. 12, 2020, the entire contents of which are incorporated herein by reference.

TECHNICAL FIELD

The present disclosure relates to an arrangement for polymerase chain reaction (PCR) with multi-channel fluorescence measurement and to a corresponding method.

BACKGROUND

PCR is a widespread analysis method in the field of biotechnology and molecular biology and makes it possible, for example by using suitable thermocyclers, to examine a plurality of samples, in particular simultaneously. Microtiter plates, in which a plurality of samples can be arranged in a sample carrier, are generally used as sample carriers.

Thermocyclers offer the possibility of performing thermally controlled process steps with different temperature cycles independently and automatically. In addition, so-called "real-time thermocyclers," which serve to carry out quantitative real-time PCR, have become known. Such devices are equipped with additional optical modules for measuring fluorescence. This enables a quantification of the reaction products obtained in real time. For the fluorescence measurement, suitable fluorescent dyes are used, which indicate an increased fluorescence when the desired reaction product is formed, or which are bound terminally to special probes and are each changed during the desired reaction in such a manner that increased fluorescence occurs. The fluorescence measurements are then typically carried out after each temperature cycle in all samples to be examined in phases of constant temperature and are graphically represented, for example. In doing so, different dyes and/or probes can also be used in each case. In this case, a distinction can be made on the basis of the different emission spectra. This is also known as "fluorescence multiplexing."

Various different devices for performing real-time PCR, which allow the detection of fluorescence at one or more different excitation and emission wavelengths, have become known from the prior art. Depending on the device used, simultaneous observation of all samples of a two-dimensional arrangement of samples, for example by means of an imaging method, or a sample multiplexing, is realized, for example.

To manage ever higher amounts of sample, the thermocyclers are optimized in such a manner that the necessary number of temperature cycles can be handled in as short a time as possible. This means that the heating and cooling phases along with the phases of constant temperature are shortened ever further (so-called rapid PCR). As a result, however, the time intervals for performing fluorescence measurements also become shorter and shorter.

Thus, DE 10 2006 036 171 A1 discloses an arrangement and a method for rapid, multi-channel fluorescence measurement in PCR samples, which enables the measurement of the fluorescence in a plurality of color channels within a short time in a plurality of samples. A rotating arrangement of the optical modules ensures rapid switching of the individual wavelengths. On the sample side, an object scanner is used, by means of which the fluorescence measurements can be carried out successively for a plurality of samples, which measurements are additionally synchronized with the respective temperature cycle. With such an arrangement, however, in each case only one sample carrier in the form of a microtiter plate can be analyzed, which can run through only one temperature cycle.

SUMMARY

An object of the present disclosure is therefore to enable rapid fluorescence measurement even for devices that can run through a plurality of independent temperature cycles.

This object is achieved by the arrangement and method according to the present disclosure.

With regard to the arrangement, the object underlying the present disclosure is achieved by an arrangement for PCR with multi-channel fluorescence measurement, comprising:
  two heating elements each having a sample receptacle for receiving one sample carrier each, wherein the sample receptacles each have a plurality of cavities arranged in rows and columns;
  two measuring heads which are each movable relative to the heating elements, wherein each measuring head is designed such that, by means of the measuring head, light can be coupled into each of the cavities in a column of the respective sample carrier and fluorescent light can be coupled out from the cavities in the column; and
  a fluorescence unit with a carrier in the form of a rotatable disk,
  at least one optical module which is arranged at least partially on the carrier and which serves for generating excitation light having at least one predeterminable wavelength, and a detection unit for detecting a fluorescence in the cavities, and
  a coupling module, which in each case has a receptacle for at least one light guide for guiding the excitation light from the fluorescence unit to the measuring heads and for guiding the fluorescence light from the measuring heads to the fluorescence unit.

Thus, the sample receptacles each form a two-dimensional arrangement for receiving a plurality of samples, which can be arranged, for example, on a sample carrier in the form of a microtiter plate with a plurality of cavities for receiving a sample in each case. The measuring heads are movable laterally and/or vertically relative to the respective sample carrier, for example, and each serve to scan one sample carrier each. For example, each of the measuring heads can be moved successively across the different columns of the two-dimensional arrangement, i.e., row by row.

The optical module is, in particular, an at least partially exchangeable assembly. The optical module has, for example, a light source, various filters, such as a fluorescence excitation filter and/or a fluorescence emission filter, lenses and/or beam splitters. In this connection, reference is made to the optical modules known from the prior art in many different embodiments, which can all also be used for the present disclosure. With regard to the detection unit, reference is also made to the variants known per se from the prior art. The detection unit is a photomultiplier, for example. The light guide can in turn be, for example, an optical fiber or a fiber bundle.

The measuring heads have, for example, a mechanical unit with a frame, which has a carrier plate, and a slide which is movable in guides, in particular driven by a motor.

According to the present disclosure, measuring heads independent of one another are used for the different heating elements with the different sample carriers, which can run through different temperature cycles, all of which can be synchronized with a common fluorescence unit. The individual measuring heads can also operate independently of one another in time. This considerably reduces the expenditure in terms of devices since only one cost-intensive fluorescence unit is necessary.

In one embodiment, at least two optical modules are arranged, in particular circumferentially distributed, on the carrier along a circular path on the rotating disk. In this manner, fluorescence measurement with a plurality of color channels is realized.

A further embodiment includes the fluorescence unit having a device for determining a number of revolutions of the carrier. Alternatively, a quantity that can be derived from the number of revolutions, such as an angular velocity, can also be ascertained. On the basis of the number of revolutions, it is possible to ascertain the relative position of the disk or the respective relative position of each of the optical modules.

In this connection, it is advantageous if the device comprises an optocoupler and a switching element, in particular a switching lug, arranged on the disk. This arrangement makes it possible to ascertain the number of revolutions in a particularly simple manner.

In one embodiment, the arrangement comprises a temperature sensor for determining and/or monitoring a temperature of at least one of the heating elements and/or sample carriers. Preferably, at least one temperature sensor is provided for each of the heating elements or sample carriers.

Finally, another embodiment of the arrangement includes arranging the coupling module relative to the carrier such that, during one complete revolution of the disk, excitation light from each optical module arranged on the carrier passes successively into each of the measuring heads and fluorescence light from each measuring head passes successively to each optical module. Accordingly, the coupling module is arranged relative to the rotating disk in such a manner that it comes into contact with each of the optical modules, or in such a manner that excitation light can be coupled into the light guides by means of each of the optical modules.

In this connection, it is conceivable on the one hand that a length of the coupling module tangential to the rotating disk is adapted to a circular arc formed by the circular radii of two adjacent optical modules, wherein the length is in particular smaller than a circular chord of the circular radii of two adjacent optical modules. Such an arrangement avoids excitation light reaching the coupling unit by means of two different optical modules at the same point in time. Such an embodiment is particularly advantageous if the disk is rotated at a constant rotating speed.

On the other hand, the coupling module can also be designed to be movable radially with respect to the rotating disk. In this case, the rotating disk and the coupling module are movable.

An object underlying the present disclosure is furthermore achieved by a method for PCR with multi-channel fluorescence measurement, comprising the following method steps:

coupling excitation light in each case into cavities of a column of a two-dimensional arrangement of a plurality of cavities of at least two sample carriers by means of a respective measuring head, detecting the fluorescence from the cavities of the respective column of the respective sample carrier, and step by step laterally moving each of the measuring heads across the columns of the two-dimensional arrangement of the cavities of each sample carrier in order to excite to fluorescence all samples of each sample carrier located in the two-dimensional arrangement of the cavities and to detect the fluorescence.

Excitation light is thus simultaneously coupled into the at least two different measuring heads, which serve to scan at least two different sample carriers, which can also run through different temperature cycles. A plurality of different sample carriers each having a plurality of samples can thus be examined with regard to the fluorescence by means of a single fluorescence unit.

The method is preferably used for an arrangement according to the present disclosure according to at least one of the described embodiments.

In one embodiment of the method, a step-by-step lateral movement of each measuring head is selected as a function of a rotational speed of a rotating disk, on which at least one optical module, preferably at least two optical modules, is arranged for generating the excitation light. The optical modules and the rotating disk are part of the fluorescence unit. The samples, which are each arranged in a row of the respective sample carrier, can thus each be scanned completely before a change is made between two different optical modules within the fluorescence unit.

In this connection, it is advantageous if the step-by-step lateral movement is carried out after a complete revolution of the rotating disk. This ensures that the respectively examined row of samples in each of the sample carriers has in each case been examined by means of all color channels, before the respectively following row of samples in each of the sample carriers is excited to fluorescence.

It is furthermore advantageous if a duration of the lateral movement of each of the measuring heads between two consecutive rows corresponds to a duration for a complete revolution of the disk. In this manner, the lateral movement of the measuring heads can be synchronized in a simple manner with the rotational speed of the rotating disk.

In a further embodiment of the method, there is a check of whether a predetermined temperature of a heating element and/or of the sample carrier has been reached, wherein a detected fluorescence is recorded only if the predetermined temperature is reached. This avoids errors with regard to the evaluation of the measured fluorescences which arise from a specific setpoint value for the temperatures of the respective samples not yet being reached in the temperature cycle taking place in each case in a sample carrier. The fluorescence measurement is preferably carried out in phases of constant temperature during the respective temperature cycle.

In this connection, it is again advantageous if the step-by-step lateral movement of a measuring head and recording of the detected fluorescence are carried out only after reaching the predeterminable temperature.

It should be noted that the embodiments described in connection with the arrangement according to the present disclosure can also be applied mutatis mutandis to the method according to the present disclosure and vice versa.

BRIEF DESCRIPTION OF THE DRAWINGS

Further details of the present disclosure and of its advantageous embodiments are explained with reference to the following figures. The following are shown.

DETAILED DESCRIPTION

Figure 1:
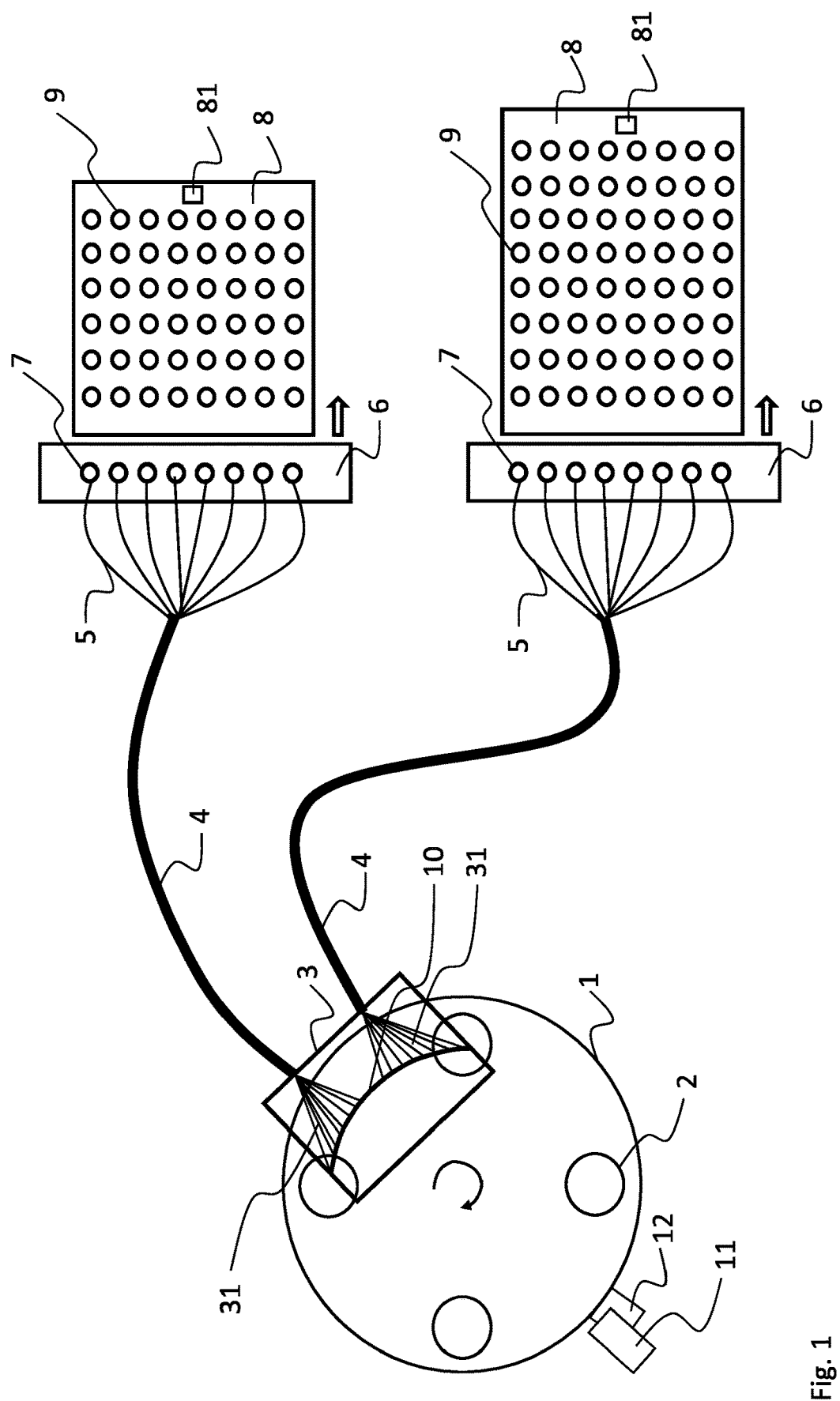
FIG. 1 shows a schematic illustration of a first possible embodiment of a device according to the present disclosure.

FIG. 1 shows a schematic illustration of a first possible embodiment of an arrangement according to the present disclosure. The arrangement here exemplarily has two heating elements 8, in which sample carriers or samples 9 are in each case arranged in rows and columns. Each heating element 8 is also assigned a respective measuring head 6, which can be moved in the direction of the arrow across the respective heating element 8. Via individual fibers 5 and lenses 7, excitation light is coupled into each sample 9 of a column and fluorescent light is coupled out. The number of fibers 5 or lenses 7 in each of the measuring heads 6 corresponds to the number of samples 9 of a row of the respective heating element 8. It should be noted that different heating elements 8 have a different number of sample receptacles and different divisions of the samples over the rows and columns. Different measuring heads 6 can correspondingly have a different number of fibers 5.

The fibers 5 are each combined in an area opposite the measuring head 6 to form a light guide 4 in the form of a fiber bundle, which is guided to a single fluorescence unit used for all measuring heads 6. The light guides 4 each terminate in a coupling module 3, which has a respective receptacle 31 for each of the light guides 4, which receptacles 31 are arranged along the circular path 10. Four different optical modules 2 are arranged in a circumferentially distributed manner on a carrier 1 so that when the disk 1 rotates, each of the optical modules 2 successively passes through the coupling module 3. In this manner, it can be ensured that each optical module 2 can individually guide excitation light to all measuring heads 6 and fluorescent light from all measuring heads 6 to the fluorescence unit during a complete revolution of the carrier 1. The length of the coupling module 3 tangential to the rotating disk 1 is thus adapted to the distances of the individual optical modules 2. In particular, the length is adapted to a circular arc 10 formed by the circular radii of two adjacent optical modules 2, here such that the length is smaller than a circular chord of the circular radii of two adjacent optical modules 2.

Furthermore, a device for determining a number of revolutions of the carrier 1 with an optocoupler 11 and a switching lug 12 is arranged on the carrier 1. The relative position of each optical module 2 relative to the coupling module 3 can thereby be ascertained in each case.

Optionally, but not shown graphically here, the heating elements 8 can have temperature sensors 81 in order to detect the temperatures of the individual heating elements 8 during the respective temperature cycles. Preferably, the fluorescence of the samples is detected only at time intervals of constant sample temperature. Different heating elements 8 can run through different temperature cycles.

Figure 2:
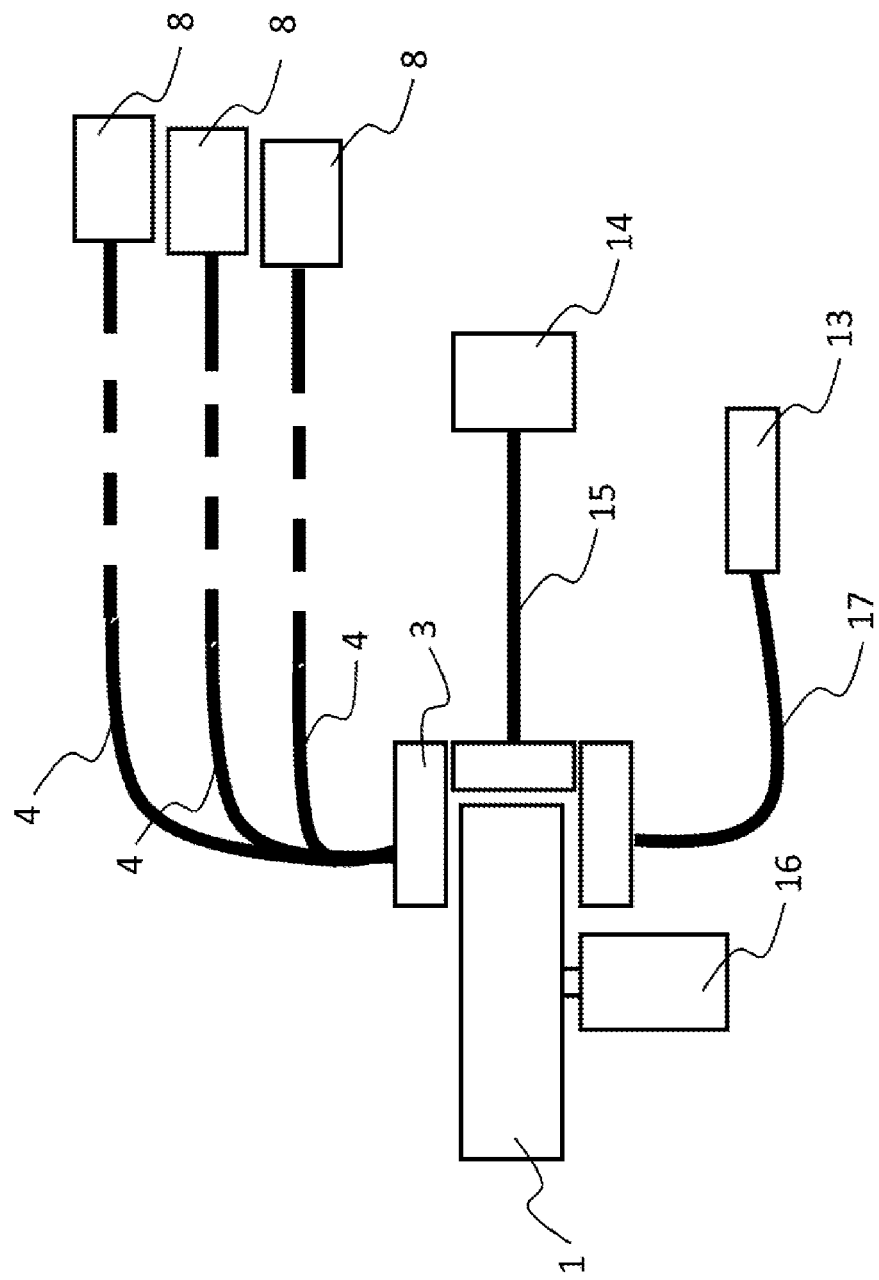
FIG. 2 shows a schematic illustration of a device according to the present disclosure with three spatially decoupled independent sample arrangements.

FIG. 2 shows a detailed illustration of the fluorescence unit. The fluorescence unit comprises a light source 14 from which excitation light is coupled into the individual measuring heads 6 via a light guide 15 in the form of a fiber bundle. Fluorescent light detected from the samples 9 is simultaneously guided via a light guide 17 to a detection unit 13, where it is converted into electrical signals and forwarded to an evaluation electronics unit which is not shown separately here.

For the example shown here, the carrier 1 is driven by means of a motor 16 and preferably rotated at a constant rotating speed. After a complete revolution of the carrier 1, all samples 9 of a column of the sample carrier have been excited to fluorescence by all the optical modules 2 present so that a lateral movement of the measuring heads 6 to the respective next column of the sample carrier can take place. In this connection, the device 11, 12 for determining a number of revolutions of the rotating disk 1 supplies a trigger signal which is used for synchronizing the scanning steps or the lateral movement of the measuring heads 6 and for assigning the respective signals reaching the detector unit 13. This control process can take place, for example, in a computation unit which is likewise not shown here.

Figure 3:
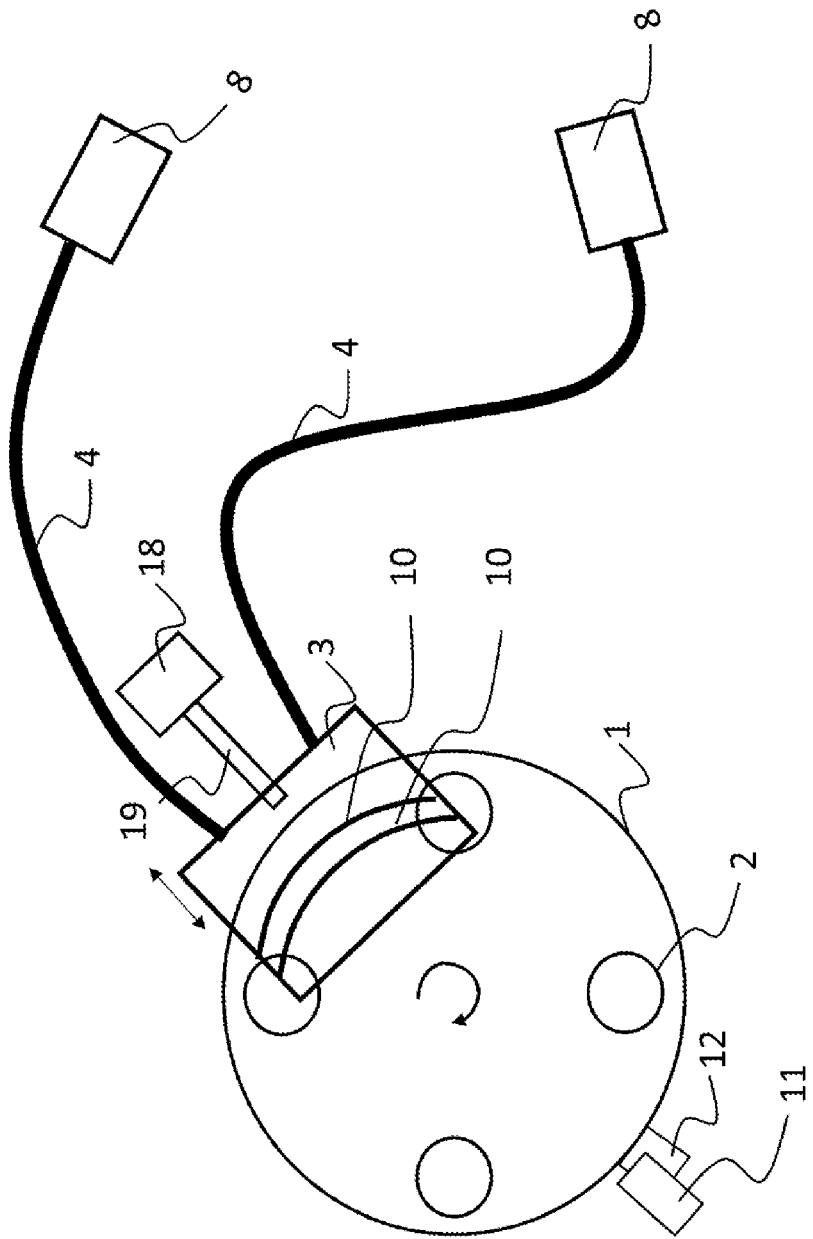
FIG. 3 shows a schematic illustration of a device according to the present disclosure with two independent sample arrangements and a movable coupling module.

A second exemplary embodiment of an arrangement according to the present disclosure is outlined in FIG. 3. The fluorescence unit is designed as shown in FIG. 1. In contrast to FIG. 1, the coupling module 3 in the case of FIG. 3 is movable radially with respect to the carrier 1 in the direction of the arrow drawn. The movement can be accomplished by a motor 18, similarly to the case of the carrier 1.

The invention claimed is:

1. An arrangement for polymerase chain reaction with multi-channel fluorescence measurement, the arrangement comprising:
    two heating elements, each including a sample receptacle configured to receive one sample carrier, wherein the sample carriers each include a plurality of cavities arranged in rows and columns;
    two measuring heads, which are each movable relative to the heating elements, wherein each measuring head is configured such that excitation light is coupled into each cavity in a column of the respective sample carrier and fluorescence light is coupled out from each cavity in the column;
    a fluorescence unit, comprising:
        a rotatable carrier;
        at least one optical module disposed at least partially on the carrier and configured to generate excitation light having at least one predeterminable wavelength; and
        a single detection unit adapted to detect the fluorescence light from the plurality of cavities of each sample carrier; and
    a coupling module including a coupling receptacle configured to receive at least one light guide configured to guide the excitation light from the fluorescence unit to each measuring head and to guide the fluorescence light from each measuring head to the fluorescence unit and to the single detection unit therein.

2. The arrangement of claim 1, wherein at least two optical modules are arranged circumferentially on the carrier along a circular path of the rotatable carrier.

3. The arrangement of claim 1, wherein the fluorescence unit includes a device configured to determine a number of revolutions of the carrier.

4. The arrangement of claim 3, wherein the device comprises an optocoupler and a switching element disposed on the carrier.

5. The arrangement of claim 1, further comprising a temperature sensor adapted to determine and/or monitor a temperature of at least one of the heating elements and/or the sample carriers.

6. The arrangement of claim 2, wherein the coupling module is disposed relative to the carrier such that, during one complete revolution of the carrier, excitation light from each optical module arranged on the carrier passes successively into each measuring head and such that the fluorescence light from each measuring head passes successively to each optical module.

7. The arrangement of claim 6, wherein a length of the coupling module tangential to the carrier is configured as a circular arc defined by circular radii of two adjacent optical modules, wherein the length is less than a circular chord of the circular radii of the two adjacent optical modules.

8. The arrangement of claim 6, wherein the coupling module is movable radially with respect to the carrier.

9. The arrangement of claim 1, wherein the rotatable carrier is disk-shaped.

* * * * *